US009248105B2

(12) United States Patent
Audett

(10) Patent No.: US 9,248,105 B2
(45) Date of Patent: *Feb. 2, 2016

(54) MULTILAMINATE BACKING CONSTRUCTION

(71) Applicant: ALZA Corporation, Vacaville, CA (US)

(72) Inventor: Jay Douglas Audett, Somerset, NJ (US)

(73) Assignee: ALZA Corporation, Vacaville, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/734,604

(22) Filed: Jun. 9, 2015

(65) Prior Publication Data

US 2015/0265548 A1 Sep. 24, 2015

Related U.S. Application Data

(63) Continuation of application No. 11/842,048, filed on Aug. 20, 2007, now Pat. No. 9,078,833, which is a continuation of application No. 10/646,539, filed on Aug. 22, 2003, now abandoned.

(60) Provisional application No. 60/407,126, filed on Aug. 30, 2002.

(51) Int. Cl.
*A61K 9/14* (2006.01)
*A61K 9/70* (2006.01)
*A61K 9/00* (2006.01)
*A61F 13/02* (2006.01)

(52) U.S. Cl.
CPC ............ *A61K 9/7092* (2013.01); *A61F 13/0276* (2013.01); *A61K 9/0014* (2013.01); *A61F 2013/0296* (2013.01)

(58) Field of Classification Search
None
See application file for complete search history.

(56) References Cited

U.S. PATENT DOCUMENTS

| 3,928,099 A | 12/1975 | Ohotsubo et al. |
| 4,334,530 A | 6/1982 | Hassell |
| 4,485,133 A | 11/1984 | Ohtsuka et al. |
| 4,751,087 A | 6/1988 | Wick |
| 4,758,434 A | 7/1988 | Kydonieus et al. |
| 4,904,475 A | 2/1990 | Gale et al. |
| 5,149,538 A | 9/1992 | Granger et al. |
| 5,314,421 A | 5/1994 | Leuenberger |
| 5,484,603 A | 1/1996 | Holden et al. |
| 5,507,525 A | 4/1996 | Leuenberger |
| 5,583,171 A | 12/1996 | Schwarz et al. |
| 5,785,991 A | 7/1998 | Burkoth et al. |
| 5,843,468 A | 12/1998 | Burkoth et al. |
| 5,871,829 A | 2/1999 | Nishizawa et al. |
| 5,879,701 A | 3/1999 | Audett et al. |
| 5,882,676 A | 3/1999 | Lee et al. |
| 5,906,830 A | 5/1999 | Farinas et al. |
| 6,004,578 A | 12/1999 | Lee et al. |
| 6,007,837 A | 12/1999 | Enscore et al. |
| 6,080,421 A | 6/2000 | Steinborn et al. |
| 6,162,858 A | 12/2000 | Auguste et al. |
| 6,210,704 B1 | 4/2001 | Sasaki et al. |
| 6,255,552 B1 | 7/2001 | Cummings et al. |
| 9,078,833 B2 * | 7/2015 | Audett |
| 2004/0043171 A1 | 3/2004 | Audett |
| 2007/0281027 A1 | 12/2007 | Audett |

FOREIGN PATENT DOCUMENTS

| DE | 19724871 | 12/1997 |
| EP | 0193938 | 3/1986 |
| EP | 250125 | 6/1987 |
| EP | 0237263 | 9/1987 |
| EP | 0309073 | 5/1988 |
| EP | 331392 | 2/1989 |
| EP | 1534508 | 12/2008 |
| FR | 2249148 | 6/1975 |
| GB | 1454218 | 12/1974 |
| GB | 2115702 | 2/1983 |
| JP | 55-6536 | 1/1980 |
| JP | Sho/61-254342 | 11/1986 |
| JP | 02/1283 | 1/1990 |
| JP | Hei/03-004570 | 1/1991 |
| JP | Hei/06-506128 | 7/1994 |
| JP | Hei/07-124244 | 5/1995 |
| JP | 08-81364 | 3/1996 |
| JP | 08-502952 | 4/1996 |
| JP | 10-067652 | 3/1998 |
| JP | 10-216239 | 8/1998 |
| JP | 11-060474 | 3/1999 |
| JP | 2000-201966 | 7/2000 |
| JP | 2000-509734 | 8/2000 |
| JP | 2000-514065 | 10/2000 |
| JP | 2001-146665 | 5/2001 |
| JP | 2002-000634 | 1/2002 |
| JP | 2002-504070 | 2/2002 |
| JP | 2002-178427 | 6/2002 |
| WO | WO 88/09169 | 12/1988 |
| WO | WO 92/16202 | 10/1992 |
| WO | WO 93/23025 | 11/1993 |
| WO | WO 97/10812 | 3/1997 |
| WO | WO 97/21430 | 6/1997 |
| WO | WO 98/00118 | 1/1998 |
| WO | WO 98/37870 | 9/1998 |
| WO | WO 00/59483 | 10/2000 |
| WO | WO 2004/020189 | 3/2004 |

OTHER PUBLICATIONS

International Search Report issued Jan. 29, 2004 in Application No. PCT/US03/26545.

(Continued)

*Primary Examiner* — Hasan Ahmed
(74) *Attorney, Agent, or Firm* — Stoel Rives LLP; Zhi-Xiang (Alex) Oh

(57) ABSTRACT

A novel backing construction for a transdermal drug delivery system is disclosed. In particular, the invention relates to a system and method for labeling a transdermal drug delivery system, wherein the backing layer contains a writable medium capable of inkless printing.

20 Claims, 2 Drawing Sheets

(56) References Cited

OTHER PUBLICATIONS

Written Opinion issued Apr. 21, 2004 in International Application No. PCT/US2003/026545.
International Preliminary Examination Report on Patentability issued Jul. 8, 2004, in Application No. PCT/US03/26545.
First Examination Report issued Oct. 7, 2005 in European Patent Application No. 03754410.3.
Response to the First Examination Report filed Mar. 28, 2006 in European Patent Application No. 03754410.3.
Derwent Abstract of FR 2249148 A Jun. 27, 1975.
Office Action issued Oct. 28, 2005 in U.S. Appl. No. 10/646,539.
Examiner Interview Summary issued Jan. 10, 2006 in U.S. Appl. No. 10/646,539.
Miscellaneous Action issued Mar. 9, 2006 in U.S. Appl. No. 10/646,539.
Response to Office Action filed Apr. 3, 2006 in U.S. Appl. No. 10/646,539.
Examiner Interview Summary issued Apr. 4, 2006 in U.S. Appl. No. 10/646,539.
Office Action issued Aug. 15, 2006 in U.S. Appl. No. 10/646,539.
Examiner Interview Summary issued Oct. 24, 2006 in U.S. Appl. No. 10/646,539.
Response to Office Action filed Nov. 13, 2006 in U.S. Appl. No. 10/646,539.
Office Action issued Apr. 4, 2007 in U.S. Appl. No. 10/646,539.
Examiner Interview Summary issued Jun. 21, 2007 in U.S. Appl. No. 10/646,539.
Response to Office Action filed Jun. 26, 2007 in U.S. Appl. No. 10/646,539.
Final Office Action issued Aug. 7, 2007 in U.S. Appl. No. 10/646,539.
Examiner Interview Summary issued Oct. 26, 2007 in U.S. Appl. No. 10/646,539.
Response to Final Office Action filed Oct. 30, 2007 in U.S. Appl. No. 10/646,539.
Office Action issued Dec. 27, 2007 in U.S. Appl. No. 10/646,539.
Response to Office Action filed Apr. 28, 2008 in U.S. Appl. No. 10/646,539.
Final Office Action issued Jul. 28, 2008 in U.S. Appl. No. 10/646,539.
Preliminary Amendment filed Aug. 20, 2007 in U.S. Appl. No. 11/842,048.
Office Action issued Dec. 30, 2009 in U.S. Appl. No. 11/842,048.
Response to Office Action filed Mar. 30, 2010 in U.S. Appl. No. 11/842,048.
Office Action issued Jul. 9, 2010 in U.S. Appl. No. 11/842,048.
Response to Office Action filed Oct. 11, 2010 in U.S. Appl. No. 11/842,048.
Office Action issued Jun. 18, 2013 in U.S. Appl. No. 11/842,048.
Response to Office Action filed Oct. 18, 2013 in U.S. Appl. No. 11/842,048.
Office Action issued Dec. 24, 2013 in U.S. Appl. No. 11/842,048.
Response to Office Action filed Feb. 28, 2014 in U.S. Appl. No. 11/842,048.
Office Action issued Apr. 25, 2014 in U.S. Appl. No. 11/842,048.
Response to Office Action filed Aug. 6, 2014 in U.S. Appl. No. 11/842,048.
Office Action issued Nov. 18, 2014 in U.S. Appl. No. 11/842,048.
Response to Office Action filed Feb. 17, 2015 in U.S. Appl. No. 11/842,048.
Notice of Allowance issued Apr. 17, 2015 in U.S. Appl. No. 11/842,048.

* cited by examiner

MULTILAMINATE BACKING CONSTRUCTION

RELATED APPLICATIONS

This application is a continuation of U.S. application Ser. No. 11/842,048 filed Aug. 20, 2007, which is a continuation of U.S. application Ser. No. 10/646,539, filed Aug. 22, 2003, which claims the benefit of U.S. Provisional Patent Application No. 60/407,126, filed Aug. 30, 2002. This application hereby incorporates by reference the U.S. applications and provisional applications enumerated herein.

TECHNICAL FIELD

The present invention relates to a multilaminate backing construction for a transdermal drug delivery system. In particular, the invention relates to a system and method for labeling a transdermal drug delivery system, wherein the outermost layer of the multilaminate backing construction contains an embossable and writable material.

BACKGROUND OF THE INVENTION

The use of microporous materials, including films, in label application for various packaging materials, containers, stationary, blood bags, recording paper, bandages and the like has been described in great detail. The following U.S. Pat. Nos. 6,255,552; 6,162,858; 5,906,830; 5,871,829; 5,583,171; 5,507,525; 5,484,603; 5,314,421; 4,751,087; 4,334,530 and 3,928,099 describe various ways of labeling packaging materials, containers, stationary, blood bags and recording paper wherein sheet materials, e.g., microporous materials, containing additives such as inorganic powder, printing inks, swellable agents, coloring agents, fillers etc. are used to create markings, e.g., etching, scoring, printing, and writing, on the label. In general, these processes require the use of high temperatures and/or the presence of additives within the microporous film in order to display the markings on the surface.

Labeling or printing information on transdermal systems has been a challenge. For example, use of printing inks, coloring agents, solvents and other additives necessary for printing may adversely interact with the active agents within the transdermal system. To address these concerns, transdermal systems have been labeled using a process not requiring the use of inks. The backing layer of the transdermal system is labelled by a thermal embossing process. The polyolefin face of the backing material is melted under pressure to reveal the label.

Notwithstanding some success, the existing technology for labeling transdermal systems has not been entirely satisfactory. The additives in the backing layer and/or the adjacent layers can interact adversely with the active agents. Additionally the use of high temperatures to label the transdermal systems may degrade various components of the transdermal systems or cause adhesive flow beyond the perimeter of the backing. These challenges would in turn affect the potency and stability of the transdermal systems.

Further, the microporous films described previously are directly laminated to a pressure sensitive adhesive to provide labels having good adhesion. However, embossing microporous film after direct lamination to a pressure sensitive adhesive would be problematic. Embossing such microporous films would result in a poorly resolved image due to the slow intrusion of the adhesive into the opaque film layer. The slow adhesive flow into the pores, accompanied by the crushing of the pores due to embossing would render the film transparent. Further, the embossed image would be poorly resolved due to adhesive flow into the pores.

SUMMARY OF THE INVENTION

The present invention is directed to the aforementioned needs in the art, and provides a transdermal system having a multilaminate backing construction. In particular, the invention relates to a system and method for labeling a transdermal drug delivery system, wherein the outermost layer of the multilaminate backing layer contains an embossable and writeable material.

In one aspect, the invention relates to a multilaminate backing construction comprising
(a) an outer layer comprising an embossable and writable material;
(b) a tie layer, the tie layer disposed on the skin proximal surface of the outer layer; and
(c) a base layer disposed on the skin proximal surface of the tie layer.

In another aspect, the multilaminate backing construction of the invention comprises
(a) an outer layer comprising an embossable and writable material, wherein the outer layer is a microporous layer or a microfibrullar layer;
(b) a tie layer comprising a secondary drug-containing reservoir, the tie layer disposed on the skin proximal surface of the outer layer; and
(c) a base layer disposed on the skin proximal surface of the tie layer.

In another aspect, the multilaminate backing construction of the invention comprises
(a) an outer layer comprising an embossable and writable material, wherein the outer layer is a microporous layer or a microfibrullar layer, wherein the outer layer is also a drug release rate controlling means;
(b) a tie layer comprising an antagonist-containing reservoir, wherein the antagonist-containing reservoir is disposed on the skin proximal surface of the outer layer; and
(c) a base layer disposed on the skin proximal surface of the tie layer.

In another aspect, the multilaminate backing construction of the invention comprises
(a) an outer layer comprising an embossable and writable material, wherein the outer layer is a microporous layer or a microfibrullar layer;
(b) a tie layer comprising a secondary drug-containing reservoir, the reservoir comprising a beneficial agent, the secondary drug-containing reservoir being disposed on the skin proximal surface of the outer layer; and
(c) a base layer disposed on the skin proximal surface of the tie layer, wherein the base layer is a drug release rate controlling means.

In another aspect, the multilaminate backing construction of the invention comprises
(a) an outer layer comprising an embossable and writable material, wherein the outer layer is a microporous layer or a microfibrullar layer;
(b) a multilaminate tie layer, the tie layer disposed on the skin proximal surface of the outer layer, wherein the tie layer may contain a secondary drug-containing reservoir; and
(c) a base layer disposed on the skin proximal surface of the tie layer.

In additional aspects, the multilaminate backing construction of the invention comprises a base layer impermeable to the drug within the drug reservoir or the tie layer; wherein the base layer comprises a material which is insoluble in water, alcohol and organic solvents. The base layer may optionally be a multilaminate layer. In certain embodiments, the base layer may be a drug release rate controlling means, e.g., a drug release rate controlling membrane. The base layer comprises a polymer such as polyolefin laminates (Dow Chemical, Midland, Mich.), acrylonitrile copolymer films (BAREX, BP Chemicals, Koln, Germany), polyethylnapthalene (PEN), polyethylene terephthalate (PET), PET modified with adhesion improvement coatings such polyacrylates or polyesters, polyimide, polyurethane, polyethylene, metallized films and glass coated films where these films can include ethylene copolymers such as ethylene-vinyl acetate copolymer (EVA), and combinations thereof. In preferred embodiments, the base layer comprises polyester, such as PET, laminated to a polymer, such as polyurethane, polyethylene, and ethylene copolymers.

In preferred embodiments, the base layer is comprised of a polymeric material selected from the group consisting of a polyester-polyolefin material such as Scotchpak 9735 (PET-PE laminate, 3M), Mediflex 1500 (PET-pigmented EVA laminate, Mylan Technologies), Mediflex 1200 (PET-EVA laminate, Mylan Technologies); Mediflex 1000 (a translucent polyolefin film, Mylan Technologies), Medifilm 500 series (EVA membrane material, Mylan Technologies); polyethylenes such as low density polyethylene (LDPE), medium density polyethylene (MDPE), high density polyethylene (HDPE), Kapton polyimide film, and other ethylene copolymer films such as EMA, or EBA copolymer films.

In additional aspects, the multilaminate backing construction of the invention comprises an outer layer comprising an embossable and writeable material. The outer surface can be scribed with a pen, and can be embossed by applying pressure with an embossing roll before or after lamination of the multilaminate backing construction to a pressure sensitive adhesive. The outer layer comprises a breathable material comprising, porous, microporous, microfibrullar, spun-bonded, spun laced, track etched, rayon (synthetic textile fibers produced by forcing a cellulose solution through fine spinnerets and solidifying the resulting filaments), wood-pulp, spun laced polyester, coated paper products, and the like, and a combination thereof. In preferred embodiments, outer layer comprises low density polyethylene (LDPE) materials, medium density polyethylene (MDPE) materials or high density polyethylene (HDPE) materials, and the like. In preferred embodiments, the outer layer is a single HDPE layer. In additional preferred embodiments, the outer layer comprises a microporous layer selected from the group consisting of Solupor microporous UHDPE P01 film (Solupor™ manufactured by DSM Desotech, the Netherlands), microporous polypropylene, e.g. Celgard microporous PP 3401 film (Celgard™ film, Celgard, Inc., Charlotte, N.C.), RoTrac Polyester Capillary Pore Membranes (OYPHEN GmbH, Germany), spun laced polyester, polypropylene or polyethylene.

In additional aspects, the multilaminate backing construction of the invention comprises a tie layer, wherein the tie layer may be multilaminate. The tie layer is comprised of materials having a low melting point that flow easily at high temperatures to allow lamination to the outer layer. The tie layer may be formed from standard materials as known in the art. For example, the tie layer is formed from a hydrophobic, a lipophilic and/or a non-polar polymeric material, such as, ethyleneoctene copolymers such as ENGAGE 8407 (from Dupont-Dow Elastomers), ethylene-vinyl acetate copolymer (EVA), low density polyethylene (LDPE), medium density polyethylene (MDPE), non pressure sensitive formulation of styrenic block copolymer thermoplastic elastomers, and the like. In preferred embodiments, the tie layer is formed from ethyleneoctene copolymers, as described in greater detail below.

In additional aspects, the tie layer comprises a secondary drug-containing reservoir. The secondary drug-containing reservoir may contain a beneficial agent or an antagonist for the beneficial agent, wherein the antagonist is in a form that is not releasable through the base layer. The skin distal surface of the drug reservoir is disposed on the outer surface. The secondary drug-containing reservoir may be the same size as the other layers of the backing construction or the secondary drug-containing reservoir may be inset from the edge of the die cut backing construction.

In certain embodiments, the secondary drug-containing reservoir comprises the drug dispersed within a polymer, wherein the drug is substantially insoluble in the secondary drug-containing reservoir polymer. In certain embodiments, the drug is dispersed in a matrix comprising a material which substantially prevents release of the drug; or the drug is complexed with an ionic resin. In additional embodiments, the secondary drug-containing reservoir comprises the drug in a multiparticulate form, wherein each particle is individually coated with a material which substantially prevents release of the drug. In additional embodiments, the secondary drug-containing reservoir comprises beads coated with the drug, wherein the beads may be formed from glass or an inert or non-dissolvable polymer, and further wherein the coated beads are optionally coated with or dispersed in material which substantially prevents release of the drug. In preferred embodiments, the drug is an opioid antagonist selected from the group consisting of naltrexone, methylnaltrexone, naloxone, nalbuphine, nalorphine, nalorphine dinicotinate, nalmefene, nadide, levallorphan, cyclozocine and pharmaceutically acceptable salts thereof. In preferred embodiments, the antagonist is present as a salt, preferably as a hydrochloride salt of an antagonist base.

These and other embodiments of the present invention will readily occur to those of ordinary skill in the art in view of the disclosure herein.

DETAILED DESCRIPTION OF THE INVENTION

Overview:

The present invention is directed to a transdermal system having a multilaminate backing construction wherein the outermost layer of the multilaminate backing construction can be embossed and be written upon with a pen or pencil. In particular, the outermost layer of the multilaminate backing construction of the present invention contains an embossable and writable material such as a microporous or microfibrillar film, which is laminated via a tie layer to a base layer.

DEFINITIONS

In describing and claiming the present invention, the following terminology will be used in accordance with the definitions set out below.

The singular forms "a," "an" and "the" include plural references unless the context clearly dictates otherwise. Thus, for example, reference to "a polymer" includes a single polymer as well as a mixture of two or more different polymers, reference to "a permeation enhancer" includes a single permeation enhancer as well as two or more different permeation enhancer in combination, and the like.

As used herein, the term "drug release controlling means" refers to a means to control/regulate the release of a drug from the secondary drug-containing reservoir.

As used herein, the terms "drug" and "active agent" are used interchangeably and are to be construed in the broadest sense to mean any material which is intended to produce some biological, beneficial, therapeutic, or other intended effect, such as permeation enhancement, an antagonist, on the organism to which it is applied. For example, the drug may be a beneficial agent or an antagonist of the beneficial agent.

MODE OF CARRYING OUT THE INVENTION

The present invention provides a multilaminate backing construction for a transdermal drug delivery system, the outermost layer of the multilaminate backing construction having an embossable and writable material.

Figure 1:
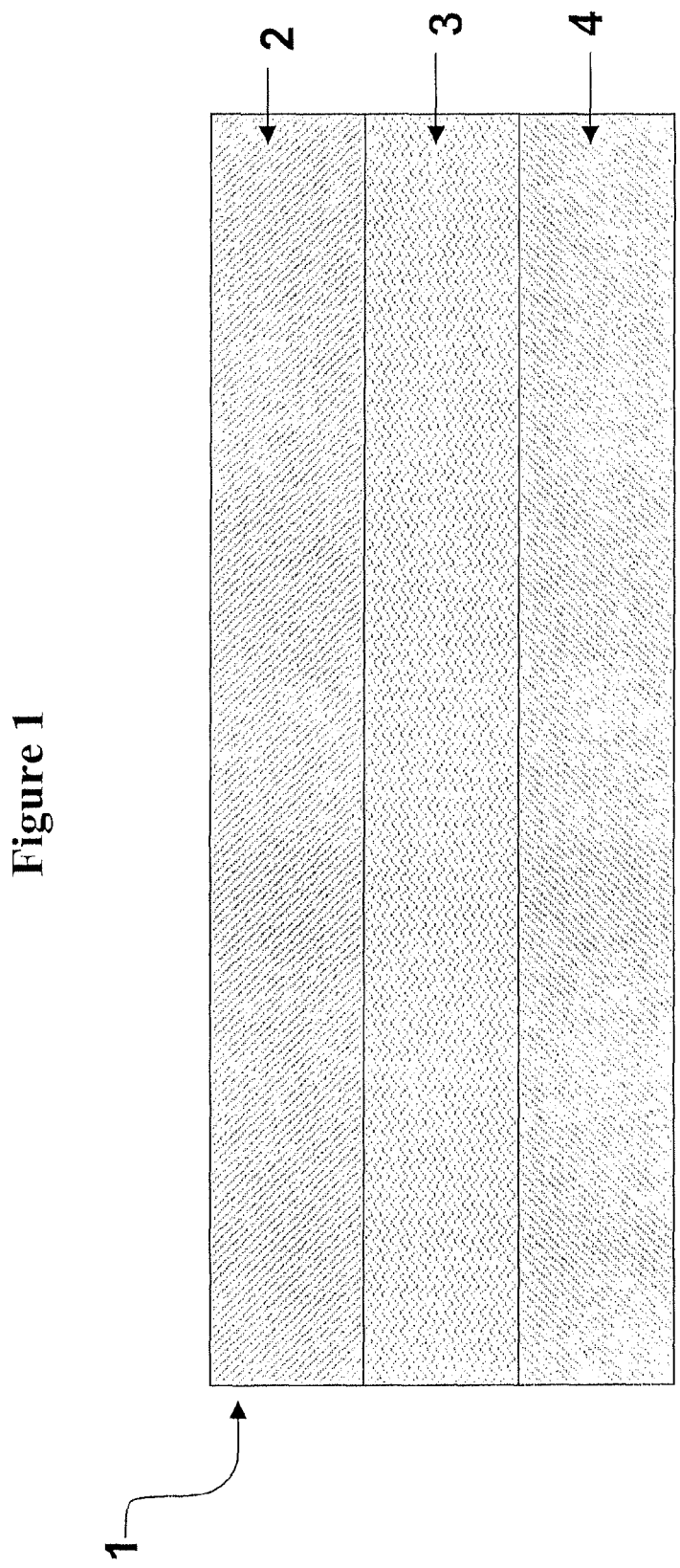
FIG. 1 illustrates a cross-section through a schematic, perspective view of one embodiment of multilaminate backing construction according to this invention.

Referring now to FIG. 1, a preferred embodiment of the multilaminate backing construction 1 according to this invention comprises an outer layer 2, a tie layer 3 wherein the skin distal surface of the tie layer is disposed on the outer layer 2, and a base layer 4 wherein the tie layer 3 is disposed on the skin distal surface of the base layer 4. In certain embodiments of the backing construction 1 of the invention, the tie layer 3 is a secondary drug-containing reservoir disposed on the skin proximal surface of the outer layer 2, and the base layer 4 is disposed on the skin proximal surface of the secondary drug-containing reservoir. The secondary drug-containing reservoir may contain a beneficial agent or an antagonist for a beneficial agent. In certain embodiments of the backing construction 1 of the invention, wherein the secondary drug-containing reservoir contains a beneficial agent, the base layer 4 is a drug rate controlling means disposed on the skin proximal surface of the secondary drug-containing reservoir. In alternative embodiments of the backing construction 1 of the invention, the secondary drug-containing reservoir contains an antagonist of a beneficial agent, and preferably, the outer layer also functions as an antagonist release rate controlling means.

Figure 2:
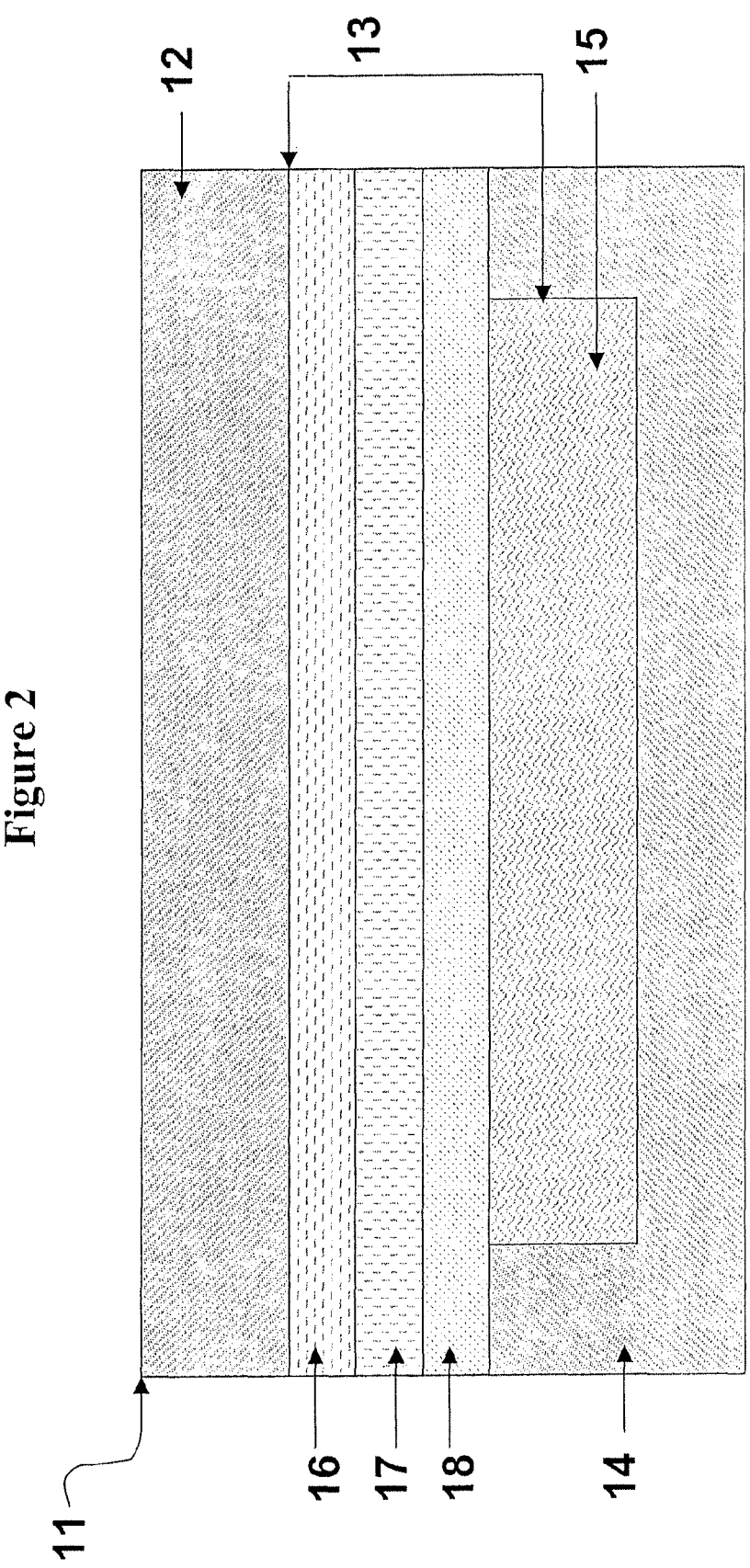
FIG. 2 illustrates a cross-section through a schematic, perspective view of another embodiment of multilaminate backing construction according to this invention.

Referring now to FIG. 2 a preferred embodiment of the multilaminate backing construction 11 according to this invention comprises an outer layer 12, a multilaminate tie layer 13 and a base layer 14. The tie layer comprises a first layer 16 disposed on the skin proximal surface of the outer layer 12; a second layer 17 disposed on the skin proximal surface of the first layer 16; a third layer 18 disposed on the skin proximal surface of the second layer 17; and a secondary drug-containing reservoir 15. The base layer 14 is configured to provide a central volume which contains the secondary drug-containing reservoir 15 in the form of a gel having dissolved or suspended drug therein. In preferred embodiments, the first layer 16 is an EVA or LDPE layer, the second layer 17 is a PET layer, the third layer 18 is an EVA, LOPE or a polyurethane layer; and the base layer 14 is a drug release rate controlling means.

The outer layer 2, 12, of the multilaminate backing construction of the invention comprises an embossable and writeable material. The outer surface can be scribed with a pen, and can be embossed by applying pressure with an embossing roll before or after lamination of the multilaminate backing construction to a pressure sensitive adhesive. The outer layer comprises a breathable material comprising, porous, microporous, microfibrullar, spun-bonded, spun laced, track etched, rayon (synthetic textile fibers produced by forcing a cellulose solution through fine spinnerets and solidifying the resulting filaments), wood-pulp, spun laced polyester, coated paper products, and the like, and a combination thereof. In preferred embodiments, outer layer comprises low density polyethylene (LDPE) materials, medium density polyethylene (MDPE) materials or high density polyethylene (HDPE) materials, and the like. In preferred embodiments, the release controlling means is a single LDPE layer. In additional preferred embodiments, the outer layer comprises a microporous layer selected from the group consisting of Solupor microporous UHDPE P01 film (Solupor™ manufactured by DSM Desotech, the Netherlands), microporous polypropylene, e.g. Celgard microporous PP 3401 film (Celgard™ film manufactured by Celgard, Inc., Charlotte, N.C.), RoTrac Polyester Capillary Pore Membranes (OYPHEN GmbH, Switzerland), spun laced polyester, polypropylene or polyethylene. The outer layer is free of any additives and is not directly laminated to a pressure sensitive adhesive. Alternatively, the outer layer can be coated with low levels of surfactants, for example, pluronic polyethylene oxide-polypropylene oxide block copolymers and the like, to provide further control over the rate of drug release from the underlying tie layer.

The outer layer 2, 12, has a thickness of about 0.012 mm (0.5 mil) to about 0.125 mm (5 mil); preferably 0.025 mm (1 mil) to about 0.1 mm (4 mil); more preferably 0.0375 mm (1.5 mil) to about 0.0875 mm (3.5 mil); and even more preferably 0.05 mm (2 mil) to about 0.0625 mm (2.5 mil).

The multilaminate backing construction according to the invention comprises a tie layer 3, 13, wherein the tie layer may be multilaminate. The tie layer is comprised of materials having a low melting point that flow easily at high temperatures to allow lamination to the outer layer 2, 12, such materials excluding pressure sensitive adhesives and HDPE. HDPE has a very high melting point and its use in the outer layer would render the embossable film prematurely clear due to high laminating temperatures and coincidental melting of the outer layer. Incorporation of pressure sensitive materials in the outer layer would result in flow of the adhesive into the pores, which would result in the embossable film prematurely turning clear. In certain embodiments, the tie layer comprises a secondary drug-containing reservoir. The secondary drug-containing reservoir may contain a beneficial agent or an antagonist for the beneficial agent. In certain embodiments, when the secondary drug-containing reservoir contains an antagonist, the outer layer also functions as a drug release rate controlling means. In certain embodiments, when the second drug-containing reservoir contains a beneficial agent, the base layer 4 is a drug release rate controlling means is disposed on the skin proximal surface of the secondary drug-containing reservoir. The secondary drug-containing reservoir may be THE same size as the other layers of the backing construction or the secondary drug-containing reservoir may be inset from the edge of the die cut backing construction. The tie layer may be formed from standard materials as known in the art. In particular, the tie layer 3, 13, is formed from low melting materials that flow easily at high temperatures and exclude pressure sensitive adhesives and HDPE. For example, the tie layer is formed from a hydrophobic, a lipophilic and/or a non-polar polymeric material, such as, ethyleneoctene copolymers such as ENGAGE 8407 (from Dupont-Dow Elastomers), ethylene-vinyl acetate copolymer (EVA), low density polyethylene (LDPE), medium density polyethylene (MDPE), styrenic block copolymer thermoplastic elastomers, PET, polyurethanes, and the like. In preferred embodiments, the tie layer is formed from ethyleneoctene copolymers, as described in greater detail below.

In certain embodiments wherein the tie layer contains a secondary drug-containing reservoir, particularly an antagonist-containing reservoir, the antagonist is dispersed in a matrix comprising a polymeric material which substantially prevents release of the antagonist, preferably a thermoformable material; or the antagonist is complexed with an ionic resin. In additional embodiments, the antagonist-containing reservoir comprises the antagonist in a multiparticulate form, wherein each particle is individually coated with a polymeric material which substantially prevents release of the antagonist, wherein the polymeric material is preferably a thermoformable material. In additional embodiments, the antagonist-containing reservoir comprises beads coated with the antagonist, wherein the beads may be formed from glass or an inert or non-dissolvable polymer, and further wherein the coated beads are optionally coated with or dispersed in a polymeric material which substantially prevents release of the antagonist, wherein the polymeric material is preferably a thermoformable material. Examples of antagonist include, but are not limited to, naltrexone, methylnaltrexone, naloxone, nalbuphine, nalorphine, nalorphine dinicotinate, nalmefene, nadide, levallorphan, cyclozocine and the like, and pharmaceutically acceptable salts thereof. Preferably, the antagonist is present as a salt.

As discussed above, the antagonist-containing reservoir comprises the antagonist dispersed within a polymer. Preferably, the antagonist is dispersed in a matrix comprising a thermoformable material which substantially prevents release of the antagonist. Alternatively, the antagonist is present in a multiparticulate form, wherein each particle is individually coated with a polymeric material which substantially prevents release of the antagonist. Preferably, the polymeric material which substantially prevents release of the antagonist is hydrophobic—i.e., substantially prevents release of the antagonist during normal use, minimizes the amount of antagonist during incidental/casual exposure to solvents (moisture e.g., sweat, during a shower), and upon ingestion or immersion in a solvent, releases the antagonist in abuse limiting amounts. Preferably, the polymeric material has a low melting point to allow processing of the antagonist in solid phase and to prevent degradation of the antagonist. Examples of a polymeric material which substantially prevents release of the antagonist include, but are not limited to, polyethylene, polyoctene, polyvinyl acetate, polymethyl acrylate, polymethyl acrylate, polyethyl acrylate, polystyrene polymers and copolymers and mixtures thereof; polystyrene copolymers such as styrenic block copolymers (SIS, SBS, SEBS), ethylene copolymers such as polyethyleneoctene copolymers, ethylene-vinyl acetate copolymer (EVA), ethylenemethyl acrylate copolymers (EMA), ethylene-acrylic acid copolymer, ethylene-ethylacrylate copolymer, and the like, and combinations thereof.

In additional embodiments, the antagonist is complexed with an ionic resin. Examples of ionic resins include, but are not limited to sulfonated polystyrene resins, and the like. Preferably the resin contains a sulfonic acid functionality which when neutralized with the antagonist base forms the sulfonate salt of the antagonist.

In additional embodiments, the antagonist-containing reservoir comprises beads coated with the antagonist, wherein the spheres or beads may be formed from glass, metals or an inert or non-dissolvable polymer, and further wherein the coated beads are optionally coated with or dispersed in a polymeric material which substantially prevents release of the antagonist, as described above. The beads may be in any shape, size or form, but are preferably small sized, preferably less than 10 microns. Examples of an inert or non-dissolvable polymer include, but are not limited to polymethylmethacrylate, polycarbonate and polystyrene.

In certain embodiments wherein the tie layer contains a secondary drug-containing reservoir, the secondary drug-containing reservoir is disposed on the skin proximal surface of the outer layer 2 and the skin distal surface of the base layer 4. The secondary drug-containing reservoir may be formed from standard materials as known in the art. For example, the secondary drug-containing reservoir is formed from a hydrophobic and/or lipophilic polymeric material, such as, hydrophobic polyurethane, ethylene-vinyl acetate copolymer (EVA) and the like.

In preferred embodiments, when the drug is a beneficial agent, the secondary drug-containing reservoir comprises about 5 to about 35 wt % of the drug; more preferably about 10 to about 35 wt % of the drug; and even more preferably about 15 to about 30 wt % of the drug. Examples of beneficial agent include, but are no limited to, fentanyl, sufentanil, risperidone, gallantamine, norelgestromin, testosterone, estradiol, nicotine, methylphenidate, fenoldopam, and the like. Preferably, the material forming the secondary drug-containing reservoir has a solubility for the drug of about 5 wt % to about 40 wt % of the total polymer composition; more preferably about 10 wt % to about 35 wt %; and even more preferably about 15 wt % to about 30 wt % of the total polymer composition.

In additional preferred embodiments, the drug is an antagonist, preferably the antagonist is in the salt form and the preferred antagonists are naltrexone, methylnaltrexone, naloxone, nalbuphine, nalorphine, nalorphine dinicotinate, nalmefene, nadide, levallorphan and cyclozocine. When the drug is an antagonist of a beneficial agent, the secondary drug-containing reservoir comprises about 20 to about 70 wt % of the drug; more preferably about 40 to about 65 wt % of the drug; and even more preferably about 50 to about 60 wt % of the drug. Preferably, the material forming the secondary drug-containing reservoir 5 has a solubility for the drug of about 0 wt % to about 1 wt % of the total polymer composition; more preferably about 0 wt % to about 0.8 wt %; and even more preferably about 0 wt % to about 0.5 wt % of the total polymer composition.

The tie layer 3, 13, including the secondary drug-containing reservoir, has a thickness of about 0.0125 mm (0.5 mil) to about 0.1 mm (4 mil), preferably about 0.015 mm (0.6 mil) to about 0.0875 mm (3.5 mil); more preferably 0.025 mm (1 mil) to about 0.08 mm (3.3 mil); and even more preferably about 0.02 mm (1.6 mil) to about 0.075 (3 mil).

In additional embodiments, the secondary drug-containing reservoir may optionally contain additional components such as, permeation enhancers, stabilizers, diluents, antioxidants, excipients, gelling agents, anti-irritants, vasoconstrictors and other materials as are generally known to the transdermal art.

Examples of permeation enhancers include, but are not limited to, fatty acid esters of glycerin, such as capric, caprylic, dodecyl, oleic acids; fatty acid esters of isosorbide, sucrose, polyethylene glycol; caproyl lactylic acid; laureth-2; laureth-2 acetate; laureth-2 benzoate; laureth-3 carboxylic acid; laureth-4; laureth-5 carboxylic acid; oleth-2; glyceryl pyroglutamate oleate; glyceryl oleate; N-lauroyl sarcosine; N-myristoyl sarcosine; N-octyl-2-pyrrolidone; lauraminopropionic acid; polypropylene glycol-4-laureth-2; polypropylene glycol-4-laureth-5dimethyl lauramide; lauramide diethanolamine (DEA). Preferred enhancers include, but are not limited to, lauryl pyroglutamate (LP), glyceryl monolaurate (GML), glyceryl monocaprylate, glyceryl monocaprate, glyceryl monooleate (GMO), and sorbitan monolaurate. Additional examples of suitable permeation enhancers are described, for example, in U.S. Pat. Nos. 5,785,991; 5,843,468; 5,882,676; and 6,004,578.

The multilaminate backing construction according to this invention comprises a base layer 4, 14, wherein the tie layer 3, 13, is disposed on the skin distal surface of the base layer 4, 14. The base layer 4, 14, may be multilaminate. The base layer 4 comprises a polymer such as polyolefin laminates (Dow Chemical, Midlane, Mich.), acrylonitrile copolymer films (BAREX, BP Chemicals, Koln, Germany), polyethylnapthalene (PEN), polyethylene terephthalate (PET), polyimide, polyurethane, polyethylene, metallized films and glass coated films where these films can include ethylene copolymers such as ethylene-vinyl acetate copolymer (EVA), and combinations thereof. In preferred embodiments, the base layer comprises a polyester such as PET laminated to a polymer such as polyurethane, polyethylene, and ethylene copolymers. In certain embodiments, the base layer may be a drug rate controlling means, as described in greater detail hereinafter. In certain embodiments wherein the secondary drug-containing reservoir contains an antagonist, the base layer 4 is impermeable to the antagonist within the secondary drug-containing reservoir; the base layer comprising a material which is insoluble in water, alcohol and organic solvents.

In preferred embodiments, the base layer is comprised of a polymeric material selected from the group consisting of a polyester-polyolefin material such as Scotchpak 9735 (PET-PE laminate, 3M), Mediflex 1500 (PET-pigmented EVA laminate, Mylan Technologies, Saint Albans, Vt.), Mediflex 1200 (PET-EVA laminate, Mylan Technologies, Saint Albans, Vt.); Mediflex 1000 (a translucent polyolefin film, Mylan Technologies, Saint Albans, Vt.), Medifilm 500 series (EVA membrane material, Mylan Technologies, Saint Albans, Vt.); polyethylenes such as low density polyethylene (LDPE), medium density polyethylene (MDPE), high density polyethylene (HDPE), ethylene methyl acrylate copolymer (EMA), ethylene ethyl acrylate copolymer (EEA), or ethylene butyl acrylate copolymer (EBA) copolymers. The base layer has a thickness of about 0.01 mm (0.4 mil) to about 0.125 mm (5 mil); preferably 0.025 mm (1 mil) to about 0.1 mm (4 mil); more preferably 0.0625 mm (1.5 mil) to about 0.0875 mm (3.5 mil); and even more preferably 0.025 mm (1 mil) to about 0.05 mm (2 mil).

The multilaminate backing construction comprises a drug release rate controlling means, preferably within the outer layer or within the base layer. In certain embodiments, when the secondary drug-containing reservoir is an antagonist-containing reservoir, the outer layer 2, 12, also functions as a drug release rate controlling means disposed on the skin distal surface of the secondary drug-containing reservoir. In alternative embodiments, when the secondary drug-containing reservoir contains a beneficial agent, the base layer 4, 14, is a drug release rate controlling means disposed on the skin proximal surface of the secondary drug-containing reservoir. In preferred embodiments, the tie layer comprises an antagonist-containing reservoir, and the outer layer is a drug release controlling means.

The rate controlling means is made of a polymeric material such as ethylene-vinyl acetate (EVA), polyvinyl chloride (PVC), ethylene-ethyl acrylate copolymer, ethylene butylacrylate copolymer, polyisobutylene (PIB), polyethylene (PE) such as low density polyethylene (LDPE), medium density polyethylene (MDPE), high density polyethylene (HDPE), and the like, and a combination thereof; the polymeric materials may be plasticized. In preferred embodiments, the base layer is a drug release rate controlling means and is adhered to the skin with an acrylic, silicone, polyisobutylene (PIB) or other pressure sensitive adhesive material. The rate controlling means has a thickness of about 0.012 mm (0.5 mil) to about 0.125 mm (5 mil); preferably 0.025 mm (0.6 mil) to about 0.1 mm (4 mil); more preferably 0.0625 mm (0.8 mil) to about 0.0875 mm (3.5 mil).

The multilaminate backing construction can be processed with less stretching under web tension because of the less extensible outer layer, preferably the Solupor layer, which also provides a surface for embossing and writing.

The transdermal devices are manufactured according to known methodology. In general, the transdermal device according to this invention comprises a backing construction 1, 11, a primary drug-containing reservoir disposed on the backing construction, wherein at least the skin contacting surface of the primary drug-containing reservoir is adhesive, and a peelable protective layer. The multilaminate backing construction is laminated via a pressure sensitive adhesive to a primary drug-containing reservoir. The primary drug-containing reservoir is typically formed from a pharmaceutically acceptable pressure sensitive adhesive but, in some cases, can be formed from a non-adhesive material. If the primary drug-containing reservoir is formed from a material that does not have adequate adhesive properties, the primary drug-containing reservoir may be formulated with a thin adhesive coating. The primary drug-containing reservoir intermediate is optionally laminated to a drug release-rate controlling membrane disposed between the primary drug-containing drug reservoir and the peelable protective layer. In subsequent operations, individual transdermal devices are die-cut, separated and unit-packaged using suitable pouchstock. Transdermal devices are cartoned using conventional equipment. The resulting transdermal delivery system provides a rate-controlled drug delivery device having embossing and writing capabilities.

Transdermal drug delivery systems having the multilaminate backing construction containing an antagonist-containing reservoir within the tie layer, when used in combination with opioid-delivering transdermal formulations, provide a deterrence to drug abusers attempting to misuse the systems, while at the same time, enable embossed labeling or scribing with a pen.

The multilaminate backing construction is embossed by application of pressure without the application of high temperatures, and without melting the outer layer. Simply applying pressure without increasing the temperature is sufficient to provide a very striking visual graphic. The method of labeling a transdermal system using the multilaminate backing construction of the invention eliminates the need for solvent-based inks when printing transdermal systems by a heat-free embossing technique. Additionally, the method of the invention eliminates adverse drug-additive interactions, improving stability, thermal sensitivity, therapeutic effects, shelf-life and ease of manufacture of a transdermal drug delivery system.

Additionally, the multilaminate backing construction of the invention is writable, allowing physicians, nurses, or users to write directly on the backing with a pen without the ink smearing. This feature is important in many clinical settings because physicians and nurses need to indicate on multiple-day transdermal systems when replacement is required. If not replaced at the appropriate time, sub-therapeutic quantities of drug may be delivered as the drug content in the system depletes.

Further, when the multilaminate backing construction is laminated to a primary drug-containing adhesive matrix, the drug cannot penetrate through the multilaminate backing construction into the heat seal layer of the pouch material due to the microporous/microfibrous nature of the outer layer.

In additional embodiments, the multilaminate backing construction is laminated to a pressure sensitive adhesive, enabling bonding to any medical device such as a blood bag, IV bag, or form-fill-seal transdermal patch, e.g. Duragesic® transdermal fentanyl delivery system.

A wide variety of materials which can be used for fabricating the various layers of the multilaminate backing construction according to this invention have been described above. This invention therefore contemplates the use of materials other than those specifically disclosed herein, including those which may hereafter become known to the art to be capable of performing the necessary functions.

Methods of Manufacture

The multilaminate backing construction of the invention are manufactured as follows. The drug-containing reservoirs are manufactured according to known methodology, as described in greater detail below.

Drug-Containing Reservoir

The secondary drug-containing reservoir can be formed by dry blending a drug, with a polymeric material, preferable a thermoformable material, at high shear and temperature using equipment such as sigma blade mixers or extruders, either batch-wise or continuously. The extrudate is calendered to the desired thickness between release liners, followed by lamination at elevated temperature to a barrier film and/or an analgesic rate controlling means. Parameters such as drug loading, drug-containing reservoir thickness, membrane selection for the rate controlling means, and surfactant modification of the rate controlling means can be varied to achieve the targeted release rate of drug, as illustrated in the Examples hereinafter. In preferred embodiments, surfactants are coated onto membrane materials forming the rate controlling means using techniques such as dip-coating, gravure coating, and the like.

In alternative embodiments, the secondary drug-containing reservoirs are manufactured according to known methodology as follows. A solution of the polymeric reservoir material, as described above, is added to a double planetary mixer, followed by addition of desired amounts of the drug, and optionally, a permeation enhancer. Preferably, the polymeric secondary drug-containing reservoir material is solubilized in an organic solvent, e.g., ethanol, ethyl acetate, hexane, and the like. The mixer is then closed and activated for a period of time to achieve acceptable uniformity of the ingredients. The mixer is attached by means of connectors to a suitable casting die located at one end of a casting/film drying line. The mixer is pressurized using nitrogen to feed solution to the casting die. Solution is cast as a wet film onto a moving siliconized polyester web. The web is drawn through the lines and a series of ovens are used to evaporate the casting solvent to acceptable residual limits. The dried secondary drug-containing reservoir film is then laminated to a selected base layer and the laminate is wound onto the take-up rolls. In another process, the secondary drug-containing reservoir can be formed using dry-blending and thermal film-forming using equipment known in the art. Preferably, the materials are dry blended and extruded using a slot die followed by calendering to an appropriate thickness. Parameters such as drug loading, secondary drug-containing reservoir thickness, drug selections, material selections and manufacturing process can be varied for preparing drug-containing reservoirs of the current invention, as illustrated in the Examples hereinafter.

The primary drug-containing reservoir is manufactured as described above using known materials and according to known procedures.

Multilaminate Backing Construction

In general, the multilaminate backing construction is manufactured as follows. For example, as illustrated in FIG. 1, the tie layer is laminated to the base layer, followed by lamination of the outer layer on the surface of the tie layer distal to the base layer at elevated temperature and pressure. Alternatively, both laminations could be conducted in a single operation by extruding the tie layer at the required width and thickness directly between the outer layer and the base layer prior to lamination. In general, the lamination is performed at a temperature ranging from about 70° C. to about 120° C., and a pressure ranging from 50 psi to about 120 psi, at the rate ranging from about 2 fpm to about 20 fpm.

In an alternative embodiment, wherein the tie layer comprises a secondary drug-containing reservoir, the multilaminate backing construction, is manufactured by laminating sequentially or simultaneously the secondary drug-containing reservoir layer to the base layer and to the outer layer under lamination conditions as described above. The secondary drug-containing reservoir is manufactured as described earlier.

In another embodiment of the multilaminate backing construction, as illustrated in FIG. 2, the tie layer is a multilaminate layer containing an outermost first layer 16 (EVA/LDPE layer) on the skin proximal surface of the outer layer, laminated to a second layer 17 (PET layer) disposed on the skin proximal surface of the first layer 16, the bi-layer is further laminated to a third layer 18 (EVA/LDPE/polyurethane layer) disposed on the skin proximal surface of the second layer 17, and a form fill type of a secondary drug-containing reservoir 15. The base layer 14, e.g. a drug release rate controlling means, is configured to provide a central volume which contains the secondary drug-containing reservoir 15 in the form of a gel having dissolved or suspended drug therein.

EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Specific examples of various multilaminate backing construction of the invention will be described in the examples set for hereinafter. In the following examples all percentages are by weight unless noted otherwise.

Example 1

A polyester-polyolefin transdermal backing material such as Scotchpak 9735 (PET-PE laminate, 3M, Cottage Grove, Minn.), Mediflex 1500 (PET-pigmented EVA laminate, Mylan Technologies, Saint Albans, Vt.), or Mediflex 1200 (PET-EVA laminate, Mylan Technologies) are laminated to Solupor microfibrous UHMW-HDPE P01 film (DSM Solutech, Heerlen, the Netherlands) at elevated temperature and pressure. The temperature required for the lamination is above the melting point of the polyolefin layer of the backing, usually above 100° C. The resulting multilaminate is used as a transdermal backing, the Solupor surface of which can be scribed with a pen, and which can be embossed by applying pressure with an embossing roll before or after lamination to a pressure sensitive adhesive.

Example 2

Mediflex 1200, a polyester-EVA laminate, is bonded to a Solupor microfibrous UHMW-HDPE film via a tie layer. The tie layer contains an ENGAGE 8407 ethylene-octene copolymer (Dupont-Dow Elastomers, DSM Solutech's) containing a naltrexone hydrochloride dispersion. Adequate bonding is achieved by performing a hot lamination step at 90 psi, 5 fpm, and 100° C. The resulting multilayered construction is laminated to a fentanyl-containing adhesive reservoir. The resulting construction is embossed for identification, can be written upon with a ballpoint pen, and contains the antagonist, naltrexone hydrochloride, to prevent fentanyl abuse.

Example 3

A multilaminate backing construction using Celgard microporous PP 3401 film (Celgard Microporous Membrane) is prepared, as described in Example 1 above.

Example 4

A multilaminate backing construction using Rotrac Capillary Pore Membrane (Oxyphen, Zug, Switzerland) is prepared, as described in Example 1 above.

Example 5

A multilaminate backing construction using Celgard microporous PP 3401 film is prepared, as described in Example 2 above.

Example 6

A multilaminate backing construction using Rotrac Capillary Pore Membrane (Oxyphen, Zug, Switzerland) microporous polyester is prepared, as described in Example 2 above.

Example 7

A translucent polyolefin film, Mediflex 1000 (Mylan Technologies, Saint Albans, Vt.), is laminated to the Solupor microfibrous film P01 via a low melting Engage 8407 ethylene-octene copolymer. The conditions required for the lamination are 80° C., 90 psi, and 3 fpm. The resulting transdermal backing material can be processed with less stretching under web tension because of the less extensible Solupor layer, which also provides a surface for embossing and writing. Further, when this backing material is laminated to a primary drug-containing adhesive matrix, drug cannot penetrate through the multi-layered backing into the heat seal layer of the pouch material because of the microfibrous nature of the Solupor layer.

Example 8

The procedure outlined in Example 7 is followed except an EVA film is substituted for the LDPE film. The resulting construction provides the benefits outlined in example 7 with the added benefit of providing an additional drug reservoir in the EVA backing layer. Drug incorporation into the EVA film is achieved during its extrusion or through the slow diffusion of drug into the EVA after lamination to an active drug-pressure sensitive adhesive reservoir.

Example 9

A LDPE or EVA membrane material such as the Medifilm 500 series from Mylan Technologies, is laminated to a polyolefin drug reservoir consisting of an EVA-40 drug dispersion, which is, in turn, laminated to the Solupor P01 film at 70° C., 50 psi, and 3 fpm on hot lamination equipment. The resulting multi-layered construction, after lamination to a pressure sensitive adhesive, provides rate-controlled drug delivery, embossing, and writing capabilities.

Example 10

Any of the multilayered constructions described in Examples 1-9 are laminated to a pressure sensitive adhesive, enabling bonding to any medical device such as a blood bag, IV bag, or form-fill-seal transdermal patch such as Duragesic transdermal fentanyl delivery system.

The above-described exemplary embodiments are intended to be illustrative in all respects, rather than restrictive, of the present invention. Thus the present invention is capable of many variations in detailed implementation that can be derived from the description contained herein by a person skilled in the art. All such variations and modifications are considered to be within the scope and spirit of the present invention.

The invention claimed is:

1. A method for transdermal administration of a drug, comprising:
   providing a transdermal drug delivery device for application on skin comprising a multilaminate backing construction disposed away from the skin relative to a primary drug-containing reservoir layer when the device is applied to the skin, the primary drug-containing reservoir layer comprising a primary drug selected from the group consisting of a therapeutic agent and an antagonist, the backing construction comprising:
   (a) an outer layer comprising an embossable, writable and breathable material,
   (b) a multilaminate tie layer disposed on the skin proximal surface of the outer layer, wherein the tie layer comprises a secondary drug-containing reservoir layer comprising a secondary drug selected from the group consisting of an antagonist and a therapeutic agent, the secondary drug being different from the primary drug, and
   (c) a base layer disposed on the skin proximal surface of the tie layer; and
   applying the device to the skin.

2. The method of claim 1, wherein the multilaminate tie layer comprises:
   (i) a first layer disposed on the skin proximal surface of the outer layer;
   (ii) a second layer disposed on the skin proximal surface of the first layer;
   (iii) a third layer disposed on the skin proximal surface of the second layer; and
   (iv) the secondary drug-containing reservoir.

3. The method of claim 2, wherein the first layer is ethylene-vinyl acetate copolymer (EVA) or low density polyethylene (LDPE) layer; the second layer is a polyethylene terephthalate (PET) layer; and the third layer is an ethylene-vinyl acetate copolymer (EVA), a low density polyethylene (LDPE), or a polyurethane layer.

4. The method of claim 1, wherein the outer layer comprises a material selected from the group consisting of low density polyethylene (LDPE), medium density polyethylene (MDPE), high density polyethylene (HDPE), ultra high density polyethylene (UHDPE), polypropylene, and polyester.

5. The method of claim 1, wherein the base layer comprises a polymeric material selected from the group consisting of polyester-polyolefin laminate, low density polyethylene (LDPE), medium density polyethylene (MDPE), high density polyethylene (HDPE), ethylene methyl acrylate copolymer (EMA), ethylene ethyl acrylate copolymer (EEA), and ethylene butyl acrylate copolymer (EBA) copolymers.

6. The method of claim 1, wherein the secondary drug-containing reservoir has a polymeric matrix including an antagonist.

7. The method of claim 1, wherein the secondary drug-containing reservoir has a thermoformable polymeric matrix including an antagonist, the antagonist being dispersed in the polymeric matrix but not dissolved in the polymeric matrix.

8. The method of claim 1, wherein the secondary drug-containing reservoir has a polymeric matrix and dispersed in the polymeric matrix is a particulate antagonist.

9. The method of claim 1, wherein the primary drug-containing reservoir further comprises an adhesive.

10. The method of claim 9, wherein the adhesive is a pressure-sensitive adhesive.

11. The method of claim 1, wherein the base layer is selected from the group consisting of (i) a layer impermeable to one or more of the primary drug and the secondary drug and (ii) a drug release rate controlling layer.

12. The method of claim 1, wherein the base layer comprises a material that is insoluble in water, alcohol, and organic solvents.

13. The method of claim 11, wherein the base layer is impermeable to one or more of the primary drug and the secondary drug.

14. The method of claim 11, wherein the base layer is a drug release rate controlling layer.

15. The method of claim 14, wherein the drug release rate controlling layer comprises a polymeric material selected from the group consisting of ethylene-vinyl acetate (EVA), polyvinyl chloride (PVC), ethylene-ethyl acrylate copolymer, ethylene butylacrylate copolymer, polyisobutylene (PIB), and polyethylene (PE).

16. The method of claim 1, wherein the outer layer comprises an embossable, writable and breathable material of porous, microporous, microfibrullar, spun-bonded, spun laced, track etched, rayon, wood-pulp, spun laced polyester, or coated paper products and combinations thereof.

17. The method of claim 1, further comprising marking the device.

18. The method of claim 17, wherein marking the device comprises writing on the outer layer.

19. The method of claim 17, wherein marking the device comprises embossing the outer layer.

20. The method of claim 1, wherein the device is applied to the skin of a human subject.

* * * * *